United States Patent [19]

Altner et al.

[11] Patent Number: 4,552,139
[45] Date of Patent: Nov. 12, 1985

[54] NARCOTICS EVAPORATOR HAVING A MONITOR EQUIPPED BY-PASS

[75] Inventors: Ulrich Altner, Bad Segeberg; H. Wolfgang Falb, Krumesse; Carl F. Wallroth, Lubeck, all of Fed. Rep. of Germany

[73] Assignee: Drägerwerk Aktiengesellschaft, Fed. Rep. of Germany

[21] Appl. No.: 596,584

[22] Filed: Apr. 4, 1984

[30] Foreign Application Priority Data

May 2, 1983 [DE] Fed. Rep. of Germany ....... 3315943

[51] Int. Cl.⁴ ............................................. A61M 11/00
[52] U.S. Cl. ............................ 128/200.14; 128/204.14
[58] Field of Search ...................... 128/200.14, 200.16, 128/200.19, 203.12, 203.25, 204.14

[56] References Cited

U.S. PATENT DOCUMENTS

| | | | |
|---|---|---|---|
| 950,738 | 3/1910 | Baker | 128/200.19 |
| 3,019,646 | 2/1962 | Gavin | 128/203.12 |
| 3,521,634 | 7/1970 | Goodyear et al. | 128/203.25 |

FOREIGN PATENT DOCUMENTS

| | | | |
|---|---|---|---|
| 57929 | 4/1967 | German Democratic Rep. | 128/203.25 |
| 638160 | 4/1962 | Italy | 128/203.25 |
| 195058 | 9/1960 | U.S.S.R. | 128/203.25 |

Primary Examiner—Henry J. Recla
Attorney, Agent, or Firm—McGlew and Tuttle

[57] ABSTRACT

In anaesthetics evaporators, the gas flow conducted through them is enriched with an anaesthetic contained in the evaporator to a desired concentration. In the anaesthetics evaporator the gas flow is divided into two part flows, the by-pass flow and the evaporating chamber flow. Both part flows are regulated by valves and regulators to obtain an exact relative flow ratio. To achieve this, this ratio must be maintained and monitored. The monitoring equipment is simple and can be retrofitted. It includes a differential pressure measuring instrument and a thermometer with a holder. The differential pressure measuring instrument is a differential pressure manometer connected via hoses and an adapter to both the inlet and outlet of the gas flow to the anaesthetics units. The thermometer to measure the evaporating temperature is fastened in well heat conducting manner to the anaesthetics evaporator by means of a holder. Temperature and differential pressure changes between inlet and outlet of the gas flow upstream and downstream of the evaporator would indicate possible changes in the part flow ratios relative to each other.

3 Claims, 3 Drawing Figures

NARCOTICS EVAPORATOR HAVING A MONITOR EQUIPPED BY-PASS

FIELD AND BACKGROUND OF THE INVENTION

This invention relates in general to anesthetics and in particular to a new and useful anaesthetics evaporator having an evaporating chamber flow conducted through an evaporating chamber and a by-pass flow conducted parallel thereto.

The invention relates to a anaesthetics evaporator with an evaporating chamber flow conducted through the evaporating chamber and a by-pass flow parallel thereto, with concentric setting and regulating devices in both lines, the regulating device compensating for the action of temperature upon the composition of the gas mixture.

In anaesthetics evaporators, the gas flow conducted through them is enriched with the anaesthetic contained in the evaporator to a desired concentration. The gas flow conducted through the anaesthetic evaporator is divided into two partial flows, the by-pass flow and the evaporating chamber flow. Both partial flows are regulated relative to each other in an exact flow ratio by valves, at least one of which is adjustable to change the concentration. The evaporating chamber flow is conducted through an evaporating chamber which generally also contains the supply of liquid anaesthetic, and enriched therein with the anaesthetic in accordance with the vapor pressure which is temperature respondent, dosed, and reunited with the similarly dosed by-pass flow which consists of the other part of the gas flow in an unaltered gas composition. The ratio of the two partial flows results in a gas mixture with the desired anaesthetics vapor concentration.

Due to the dependence of the vapor pressure on the temperature of the liquid anaesthetic there results a temperature-dependent concentration. In order to render this dependence ineffective, which would alter the mixing ratio greatly, particularly due to the heat loss originating during the evaporation, known anaesthetics evaporators have temperature compensation devices.

One known anaesthetic evaporator has a regulator, located in the by-pass and consisting of parts disposed in both the evaporating chamber flow and the by-pass flow and made of materials of different coefficients of thermal expansion, forming an annular gap in the by-pass which changes as a function of temperature. The height of the annular gap thus determines the gas flow in the by-pass (German PS 25 07 261).

SUMMARY OF THE INVENTION

The invention provides the anaesthetic evaporator with an additional monitoring device, through which the set concentration is monitored indirectly via the temperature in the evaporator and the pressure differential in the gas flow upstream and downstream of the evaporator.

It is an object of the invention to provide a anaesthetic evaporator with a by-pass paralleled to the evaporating chamber and a monitoring device to observe whether the set concentration is being maintained, the monitoring device having to be simple and retrofittable without major changes on the evaporator.

According to the invention, this problem is solved in that there is attached to the anaesthetics evaporator a monitoring device which comprises a differential pressure measuring device containing a differential pressure manometer and an adapter, connected by hoses, between gas flow inlet and outlet to the anaesthetics unit, and a thermometer with a holder.

The advantages achieved by the invention are, in particular, that retrofitting is possible without having to perform any manipulations which could affect the adjustments. A change in the pressure differential in the gas flow points, among other things, to disturbances in the division of by-pass flow and evaporating chamber flow. Attaching the adapter, the differential pressure manometer and the thermometer with its holder is simple.

Accordingly, it is an object of the invention to provide a anaesthetics evaporator having an evaporating chamber with a flow conducted through the chamber also through a by-pass which is conducted parallel thereto and including a fitting and regulating device located in the connection between the two, the regulating device compensating for the action of temperature upon the composition of the gas mixture and the regulating device comprising differential pressure measuring device which includes a differential pressure manometer and an adapter connected between the inlet and outlet of the gas flow to the anaesthetics unit and a temperature arranged in a holder attached to the unit.

A further object of the invention is to provide a anaesthetics evaporator which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
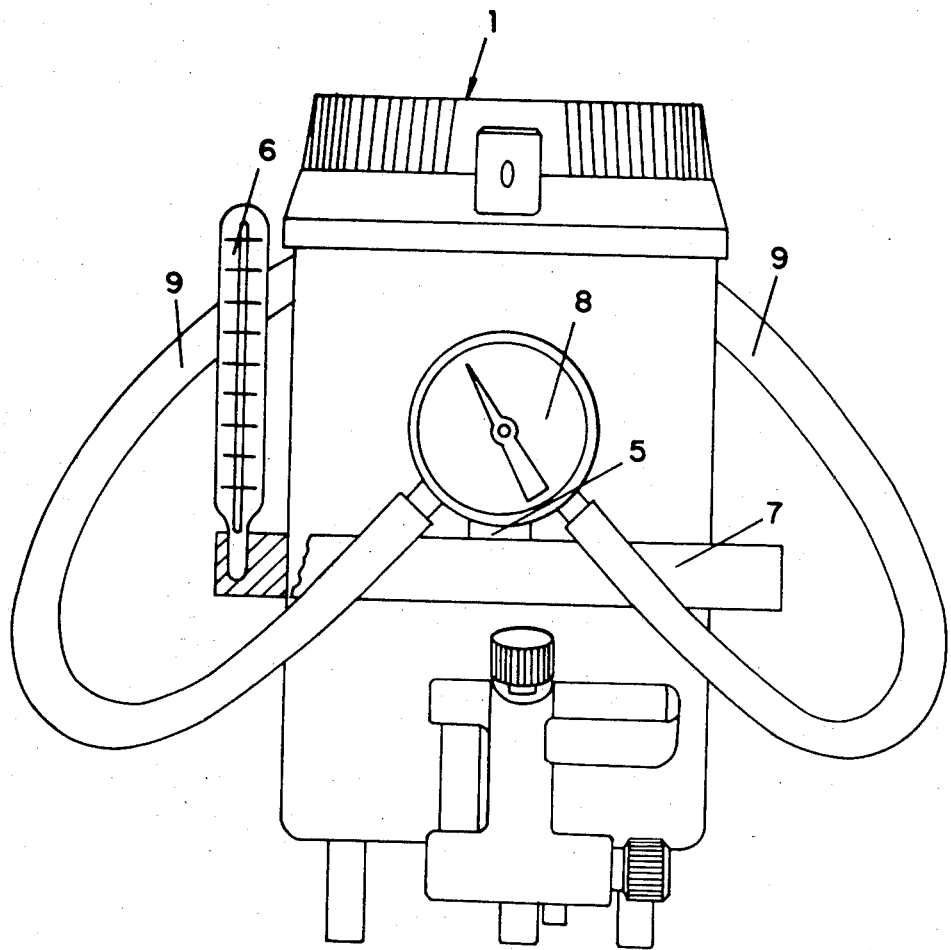
FIG. 1 is a front elevational view of a anaesthetics evaporator with retrofitted monitoring.
Figure 2:
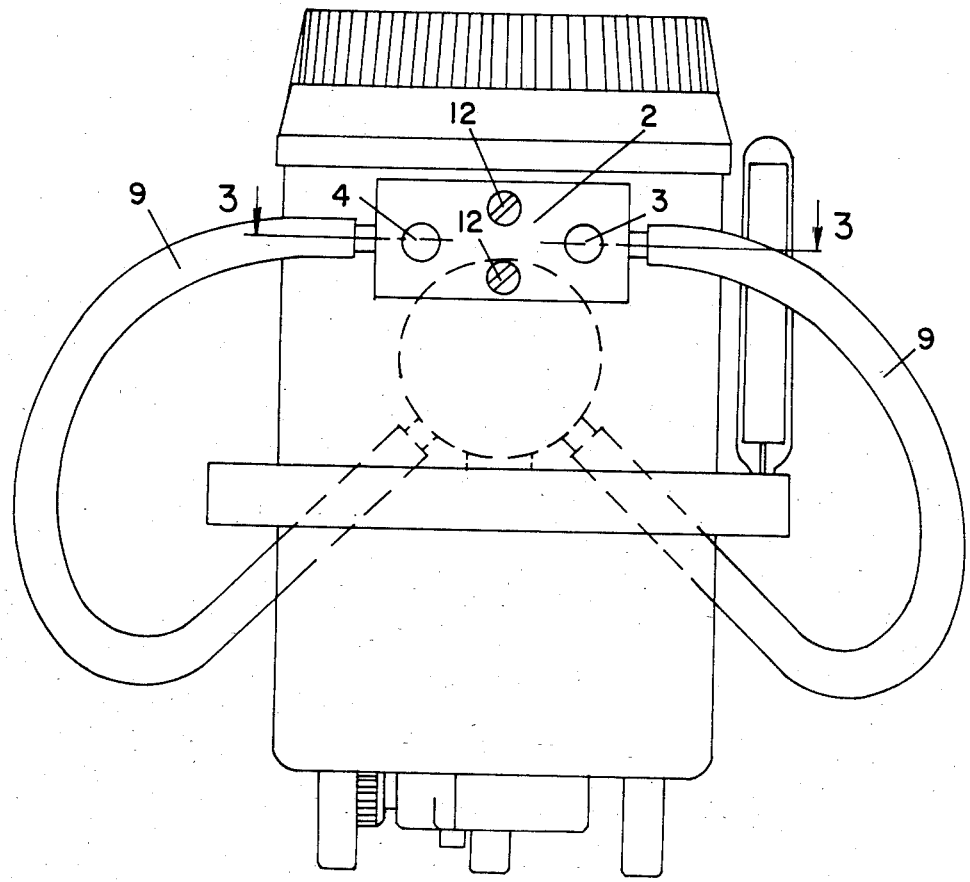
FIG. 2 is a rear elevational view.
Figure 3:
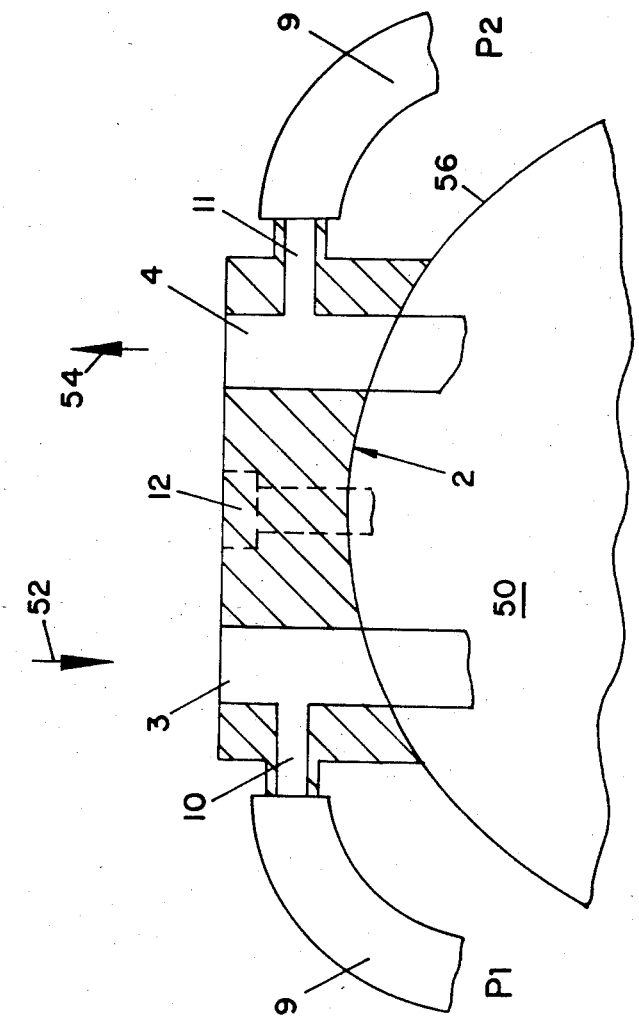
FIG. 3 the adapter.

Referring to the drawings in particular the invention embodied therein comprises a anaesthetics evaporator generally designated 1 which has an interior evaporating chamber designated 50 in FIG. 3 with a gas flow conducted into the chamber 50 to an inlet 3 in the direction of arrow 52 out through an outlet 4 in the direction of the arrow 54. In addition there is a by-pass flow which is conducted through an exterior tubing 9 and connecting fittings 10 and 11.

In accordance with the invention the setting and regulating device generally designated 2 is affixed to the housing 56 and includes connecting passages 3 and 4 forming the inlet and the outlet as well as the passages 10 and 11 for the connecting fittings for the by-pass flow to the hose 9. The device 2 is secured by screws 12 to the housing 56.

The setting and regulating device 2 is provided to compensate for the action of temperature upon the composition of the gas mixture and the regulating device includes the inlet gas flow through the duct 10 to the inlet 3 and through a duct 11 to the outlet 4. The monitoring unit includes a differential pressure mamometer 8 which is connected between the inlet 3 and the outlet 4 and a thermometer 6 which is secured to the wall 56 by means of a conductive holder 7.

The anaesthetics evaporator 1 is connected to the gas flow nipples of the anaesthetics unit via an adapter 2. The gas flow enters the evaporator 1 through the inlet 3 and leaves it again through the outlet 4.

The monitoring device consists of the differential pressure measuring instrument 5 between the inlet 3 and the outlet 4 and of the thermometer 6 with holder 7.

The differential pressure measuring instrument 5 contains a differential pressure manometer 8, connected via hoses 9 to the adapter 2 and there via a duct 10 to the inlet 3 and a duct 11 to the outlet 4. The adapter 2 is fastened to the rear of the anaesthetics evaporator 1 by means of screws 12, the differential pressure manometer 8 to the front to the holder 7 of the thermometer 6.

The adapter 2 is of flat design. The holder 7 is braced to the body of the anaesthetics evaporator 1 in well heat conducting fashion.

The monitoring function of the evaporating temperature is performed via the thermometer 6. The differential pressure manometers 8 monitors indirectly via the pressure differential $P_1-P_2$, the correct gas flow division into the by-pass flow and the evaporating chamber flow required for the concentration.

While a specific embodiment of the invention has been shown and described in detail to illustrate the application of the principles of the invention, it will be understood that the invention may be embodied otherwise without departing from such principles.

What is claimed is:

1. In a anaesthetics evaporator having an evaporating chamber with a flow into and out of the chamber, further including by-pass flow means conducted parallel to the interior flow around the exterior of the chamber, the improvement comprising an adapter mounted on the evaporator and having an inlet and an outlet passage for the gas to and from the interior of the chamber, a by-pass flow conduit connected from the inlet passage around the exterior of the chamber to the outlet passage, and including a differential pressure manometer connected in said conduit between said inlet passage and said outlet passage, and a thermometer mounted on said evaporator in heat contact relationship therewith.

2. In a anaesthetics evaporator according to claim 1, wherein said evaporator includes a housing having an exterior wall conforming to a wall of said adapter, said adapter comprising a flat block member and bolt means bolting said adapter to said housing.

3. In a anaesthetics evaporator according to claim 1, further comprising a thermometer holding means mounting said thermometer on said evaporator and wherein said thermometer holding means also secures said pressure manometer to said evaporator housing, said holding means comprising a heat conducting member in heat contact relationship with said evaporator.

* * * * *